(12) United States Patent  
Yamamoto

(10) Patent No.: US 8,074,790 B2
(45) Date of Patent: Dec. 13, 2011

(54) MANUFACTURING METHOD FOR ABSORPTIVE ARTICLE

(75) Inventor: Hiroki Yamamoto, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 377 days.

(21) Appl. No.: 12/390,124

(22) Filed: Feb. 20, 2009

(65) Prior Publication Data

US 2010/0032263 A1  Feb. 11, 2010

(30) Foreign Application Priority Data

Aug. 7, 2008 (JP) ................. P2008-204645

(51) Int. Cl.
*A61F 13/15* (2006.01)
(52) U.S. Cl. ............... 198/817; 198/689.1; 156/519; 156/543; 156/552
(58) Field of Classification Search ........... 198/626.1, 198/626.3, 626.5, 689.1, 817; 156/516, 519, 156/522, 543, 552
See application file for complete search history.

(56) References Cited

U.S. PATENT DOCUMENTS

| | | | | |
|---|---|---|---|---|
| 4,943,340 | A * | 7/1990 | Ujimoto et al. | 156/496 |
| 5,296,080 | A * | 3/1994 | Merkatoris et al. | 156/496 |
| 5,560,793 | A * | 10/1996 | Ruscher et al. | 156/73.1 |
| 6,648,122 | B1 * | 11/2003 | Hirsch et al. | 198/377.08 |
| 7,533,709 | B2 * | 5/2009 | Meyer | 156/517 |
| 7,618,513 | B2 * | 11/2009 | Meyer | 156/285 |
| 7,638,014 | B2 * | 12/2009 | Coose et al. | 156/250 |

FOREIGN PATENT DOCUMENTS

| JP | 2007-117646 A | 5/2007 |
|---|---|---|
| JP | 2008012005 A * | 1/2008 |

* cited by examiner

*Primary Examiner* — Mark A Deuble
(74) *Attorney, Agent, or Firm* — Lowe, Hauptman, Ham & Berner, LLP

(57) ABSTRACT

A manufacturing method for an absorptive article having a waistband member, includes: transporting a continuum (for example, second to seventh continuum) including waistband regions 1A and 1B corresponding to the waistband member. In the transporting, the continuum is asymmetric with respect to a center line CL of the continuum in a moving direction of the continuum, and is transported while being held on at least a first belt conveyor 110 and a second belt conveyor 120.

13 Claims, 7 Drawing Sheets

US 8,074,790 B2

MANUFACTURING METHOD FOR ABSORPTIVE ARTICLE

CROSS REFERENCE TO RELATED APPLICATIONS

This application is based upon and claims the benefit of priority from the prior Japanese Patent Application No. JP 2008-204645, filed on Aug. 7, 2008; the entire contents of which are incorporated herein by reference.

BACKGROUND OF THE INVENTION

1. Field of the Invention

The present invention relates to a manufacturing method for an absorptive article having waistband members.

2. Description of the Related Art

Heretofore, an absorptive article such as a disposable diaper has been produced on the assembly line. A manufacturing method for such absorptive articles includes: a step of transporting, by a belt conveyor, a continuum provided with at least a waistband region corresponding to the waistband member of the absorptive articles. (See Japanese Patent Application Publication No. 2007-117646 (pages. 2-4), for example.)

An example of the step of transporting the continuum includes a longitudinal feed method and a cross feed method. The longitudinal feed method is a method for transporting the continuum while its waistband front-back direction (direction from one waistband region to other waistband region) is in line with a moving direction (hereinafter, an MD direction) of the belt conveyor. Meanwhile, the cross feed method is a method for transporting the continuum while its waistband front-back direction is in line with a direction (hereinafter, a CD direction) crossing the MD direction.

SUMMARY OF THE INVENTION

Incidentally, the continuum is provided with multiple member such as an absorber, a gather (or an elastic member), and a waterproof film. Generally, the continuum (or the absorptive article) is symmetric with respect to a first center line that is a center line substantially parallel to the waistband front-back direction. However, the continuum is asymmetric with respect to a second center line that is a center line crossing the waistband front-back direction.

Here, the term "asymmetric" indicates that a difference lies at least partially in any given symmetrical locations across the second center line. For example, the term "asymmetric" includes the following differences between any given symmetrical locations across the second center line: a difference in the shape of the continuum (e.g., the shape of a leg opening region), and a difference in member disposed position, a difference in stretching property and a difference in stress.

In the above-mentioned longitudinal feed method, a center line of the continuum in the moving direction, which is passing through the center of the continuum in the moving direction, coincides with the first center line. Thus, the continuum is symmetric with respect to the center line in the moving direction. On the other hand, in the above-described cross feed method, the center line in the moving direction coincides with the second center line. Thus, the continuum is asymmetric with respect to the center line in the moving direction.

Therefore, when the continuum is transported while being asymmetric with respect to the center line in the moving direction, the continuum may not be transported stably on the belt conveyor, and either side of the center line in the moving direction may possibly be displaced, thereby the continuum may meander on the belt conveyor.

The present invention has been therefore made in consideration of the above-described problems inherent in the related art. It is an object of the present invention to provide a manufacturing method for an absorptive article, which can suppress the meandering of the continuum, when the continuum is transported while being asymmetric with respect to the center line in the moving direction.

SUMMARY OF THE INVENTION

Figure 1:
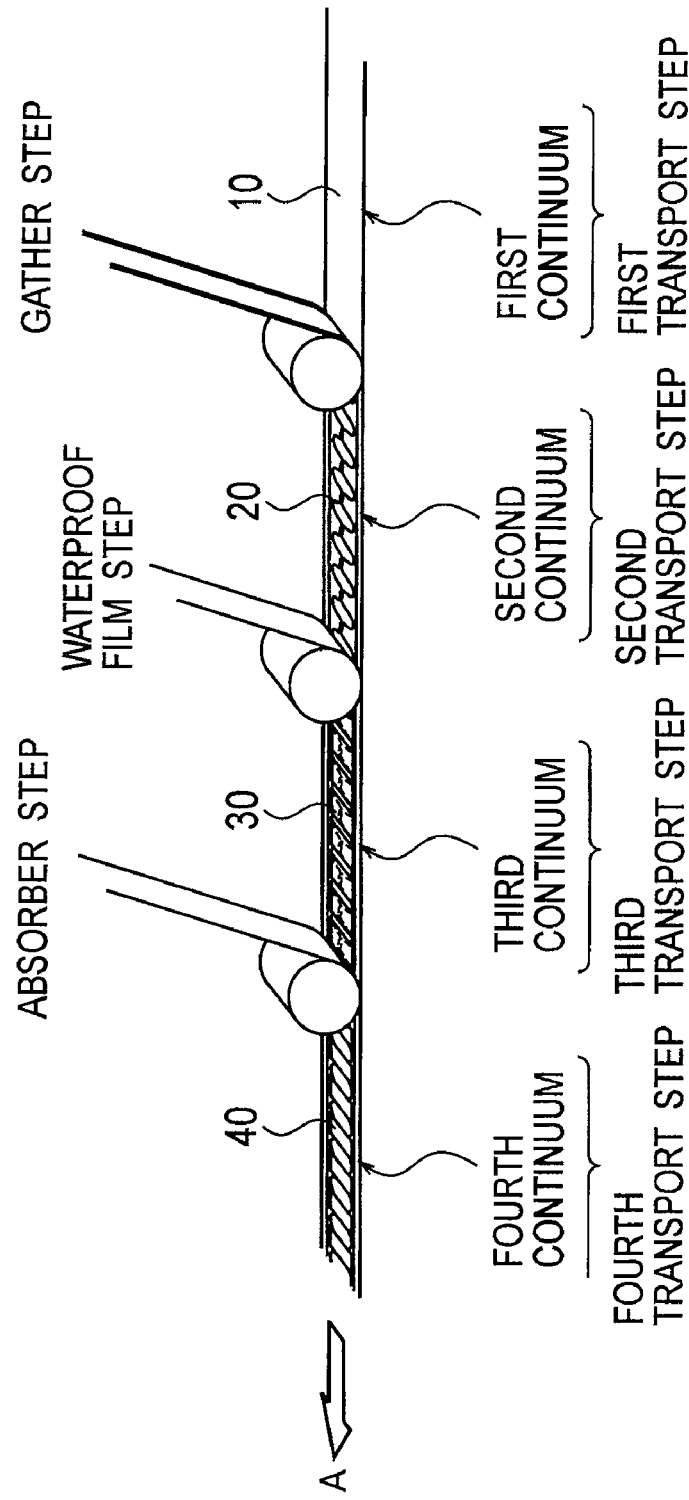
FIG. 1 is a schematic view (Part 1) showing a manufacturing method for an absorptive article according to an embodiment of the present invention.

An aspect of the present invention is summarized as a manufacturing method for an absorptive article, including: transporting a continuum (second to seventh continuums) including a waistband region (waistband regions 1A and 1B). In transporting the continuum, the continuum is asymmetric with respect to a center line (moving-direction center line CL) in a moving direction (MD direction), and is transported while being held on at least a first belt conveyor (first belt conveyor 110) and a second belt conveyor (second belt conveyor 120).

According to the present invention, it is possible to provide a manufacturing method for an absorptive article that can suppress the meandering of the continuum, when the continuum is transported while being asymmetric with respect to the center line in the moving direction

DETAILED DESCRIPTION OF THE PREFERRED EMBODIMENTS

Description will be given below with reference to the drawings with regard to embodiments of the present invention. Specifically, description will be given with regard to (1) a manufacturing method for an absorptive article, (2) a transport step, (3) a configuration of a belt conveyor, (4) operations and effects, (5) modified embodiments, and (6) other embodiments.

Incidentally, throughout the drawings, the same or similar parts are designated by the same or similar reference numerals. It should be noted that the drawings are schematic, and dimensional ratios and others therein are different from actual ones.

It is to be therefore understood that specific dimensions and others should be determined based on the following description. As the matter of course, it is also to be understood that differences may lie in the relations or ratios between dimensions in the drawings as cross-referred.

(1) A Manufacturing Method for an Absorptive Article

Figure 2:
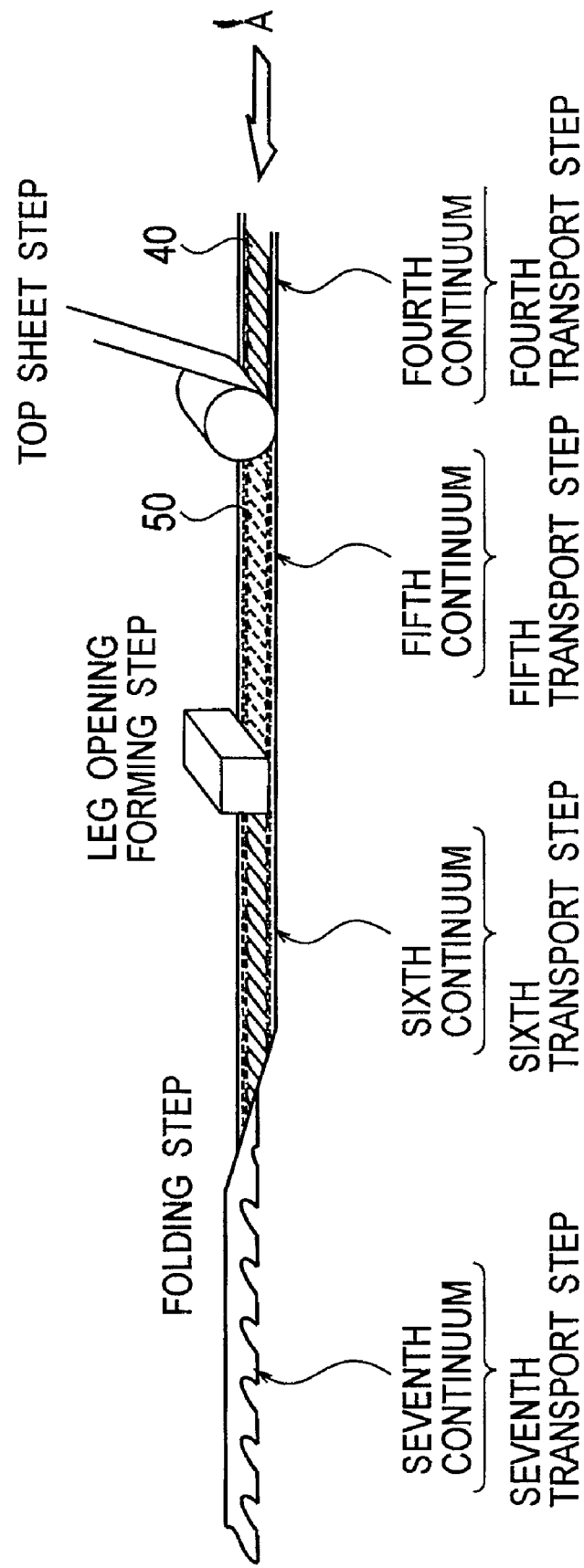
FIG. 2 is a schematic view (Part 2) showing the manufacturing method for an absorptive article according to the embodiment of the present invention.

Firstly, description will be given with reference to FIGS. 1 and 2 with regard to a manufacturing method for an absorptive article according to an embodiment of the present invention. FIGS. 1 and 2 are schematic views showing the manufacturing method for an absorptive article according to the embodiment of the present invention. An absorptive article in the embodiment of the present invention is a disposable diaper.

Incidentally, the manufacturing method for the absorptive article uses a belt conveyor 100 to be described later (see FIGS. 3 and 4); however, the belt conveyor 100 is omitted from FIGS. 1 and 2.

As shown in FIGS. 1 and 2, the manufacturing method for an absorptive article includes at least a gather step, a waterproof film step, an absorber step, a top sheet step, a leg opening forming step, and a folding step.

(1-1) The Gather Step

In the gather step, an elastic body (hereinafter, a fit gather 21) is placed on a continuum 10 of an outer sheet in waistband regions 1A and 1B (see FIGS. 3 and 4) corresponding to a waistband (or belly and back) member of the absorptive article. The fit gather 21 is placed in a moving direction (hereinafter, an MD direction) of the absorptive article.

Also, the gather step includes placing the elastic body (hereinafter, a leg gather 22) on the continuum 10 of the outer sheet in a crotch region 1C corresponding to a crotch member of the absorptive article. The leg gather 22 is placed while being swung in a direction (hereinafter, a CD direction) crossing the MD direction.

Here, the continuum 10 of the outer sheet and a gather 20 (that is, the fit gather 21 and the leg gather 22) are adhesively bonded by an adhesive such as a hot-melt adhesive. Incidentally, hereinafter, the continuum 10 of the outer sheet is called as a "first continuum," and a continuum formed of the first continuum and the gather 20 bonded together is called as a "second continuum."

(1-2) The Waterproof Film Step

In the waterproof film step, a waterproof film 30 having a printed film (that is, a film having a design of a character or a figure) laminated thereto is cut to a predetermined size. The cut waterproof film 30 is placed on top of the second continuum. The second continuum and the waterproof film 30 are adhesively bonded by an adhesive such as a hot-melt adhesive. Incidentally, a continuum formed of the second continuum and the waterproof film 30 bonded together is hereinafter called as a "third continuum."

(1-3) The Absorber Step

In the absorber step, an absorber 40, which is preformed, is cut to a predetermined size. The cut absorber 40 is placed on top of the third continuum. The third continuum and the absorber 40 are adhesively bonded by an adhesive such as a hot-melt adhesive. Incidentally, a continuum formed of the third continuum and the absorber 40 bonded together is hereinafter called as a "fourth continuum."

(1-4) The Top Sheet Step

In the top sheet step, a continuum 50 of a top sheet, to which a three-dimensional gather (not shown) for preventing a side leak is laminated, is placed on top of the fourth continuum. The fourth continuum and the continuum 50 of the top sheet are adhesively bonded by an adhesive such as a hot-melt adhesive. Incidentally, a continuum formed of the fourth continuum and the continuum 50 of the top sheet bonded together is hereinafter called as a "fifth continuum."

(1-5) The Leg Opening Forming Step

The leg opening forming step includes forming leg opening regions 1D (e.g., leg holes) located on both sides of the crotch region 1C in the fifth continuum. Incidentally, the fifth continuum having the leg opening regions 1D formed therein is hereinafter called as a "sixth continuum."

(1-6) The Folding Step

The folding step includes folding the sixth continuum in two along a center line of the sixth continuum in the moving direction (hereinafter, the center line of the continuum in the moving direction is called as a "moving-direction center line CL"). Incidentally, the sixth continuum folded in two is hereinafter called as a "seventh continuum."

(2) A Transport Step

Description will now be given with reference to FIGS. 1 and 2 with regard to the transport step according to the embodiment. As shown in FIGS. 1 and 2, in the transport step, the belt conveyor to be described later transports the first to seventh continuums between the above-mentioned steps.

Specifically, the transport step includes at least a first transport step, a second transport step, a third transport step, a fourth transport step, a fifth transport step, a sixth transport step, and a seventh transport step.

In the first transport step, the first continuum (the continuum 10 of the outer sheet) is transported by the belt conveyor 100 (a first belt conveyor 110 and a second belt conveyor 120). Incidentally, detailed description will be given later with regard to the belt conveyor 100 (see FIGS. 3 to 5).

In the second transport step, the second continuum (the first continuum and the gather 20) is transported by the belt conveyor 100 same as the belt conveyor 100 used in the first transport step.

In the third transport step, the third continuum (the second continuum and the waterproof film 30) is transported by the belt conveyor 100 same as the belt conveyor 100 used in the second transport step.

In the fourth transport step, the fourth continuum (the third continuum and the absorber 40) is transported by the belt conveyor 100 same as the belt conveyor 100 used in the second and third transport steps.

In the fifth transport step, the fifth continuum (the fourth continuum and the continuum 50 of the top sheet) is transported by the belt conveyor 100 same as the belt conveyor 100 used in the second to fourth transport steps.

In the sixth transport step, the sixth continuum (the fifth continuum having the leg opening regions 1D formed therein) is transported by the belt conveyor 100 same as the belt conveyor 100 used in the second to fifth transport steps.

In the seventh transport step, the seventh continuum (the sixth continuum folded in two) is transported by the belt conveyor 100 same as the belt conveyor 100 used in the second to sixth transport steps.

(3) The Configuration of a Belt Conveyor

Figure 3:
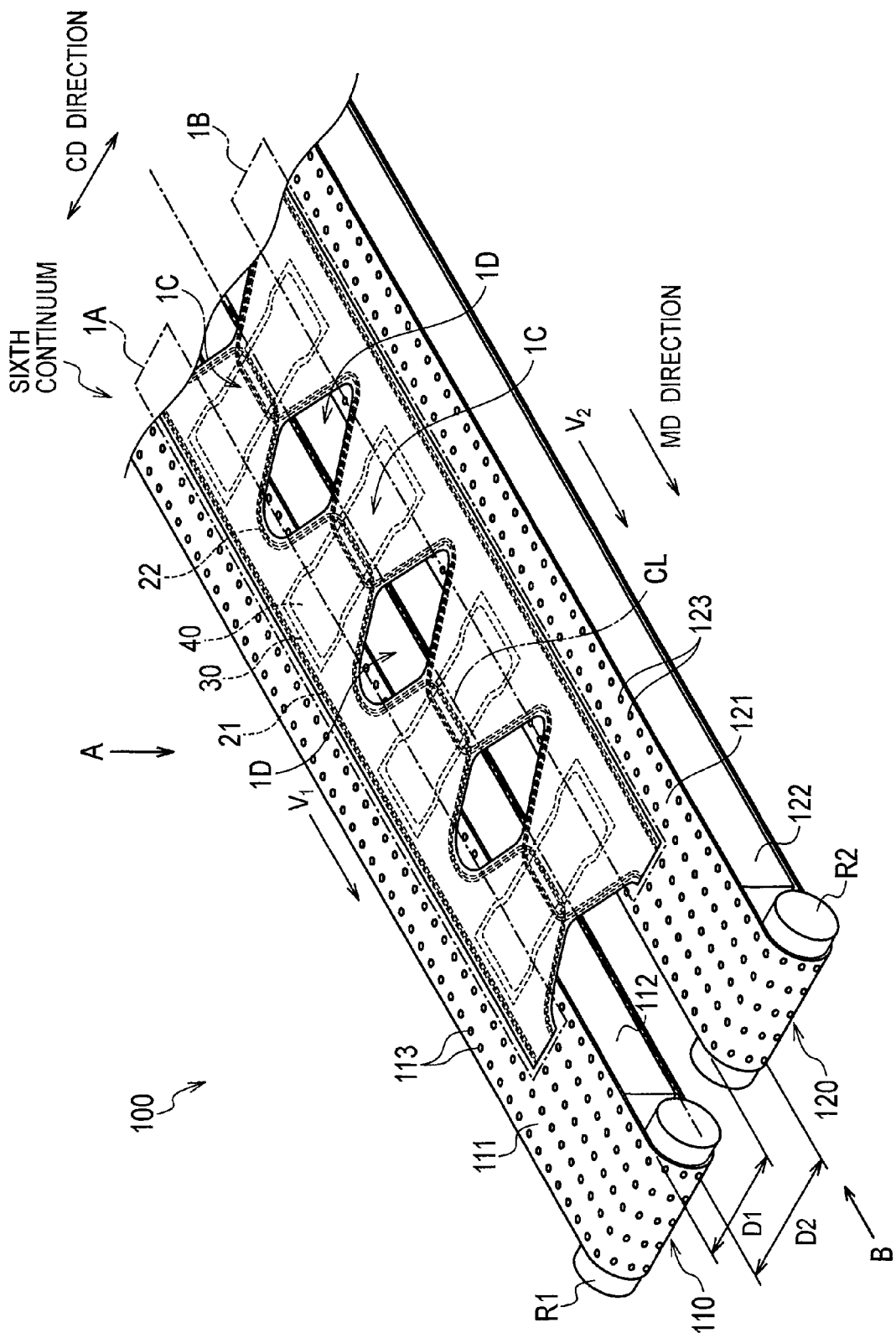
FIG. 3 is a partial perspective view showing a belt conveyor 100 according to the embodiment of the present invention.
Figure 4:
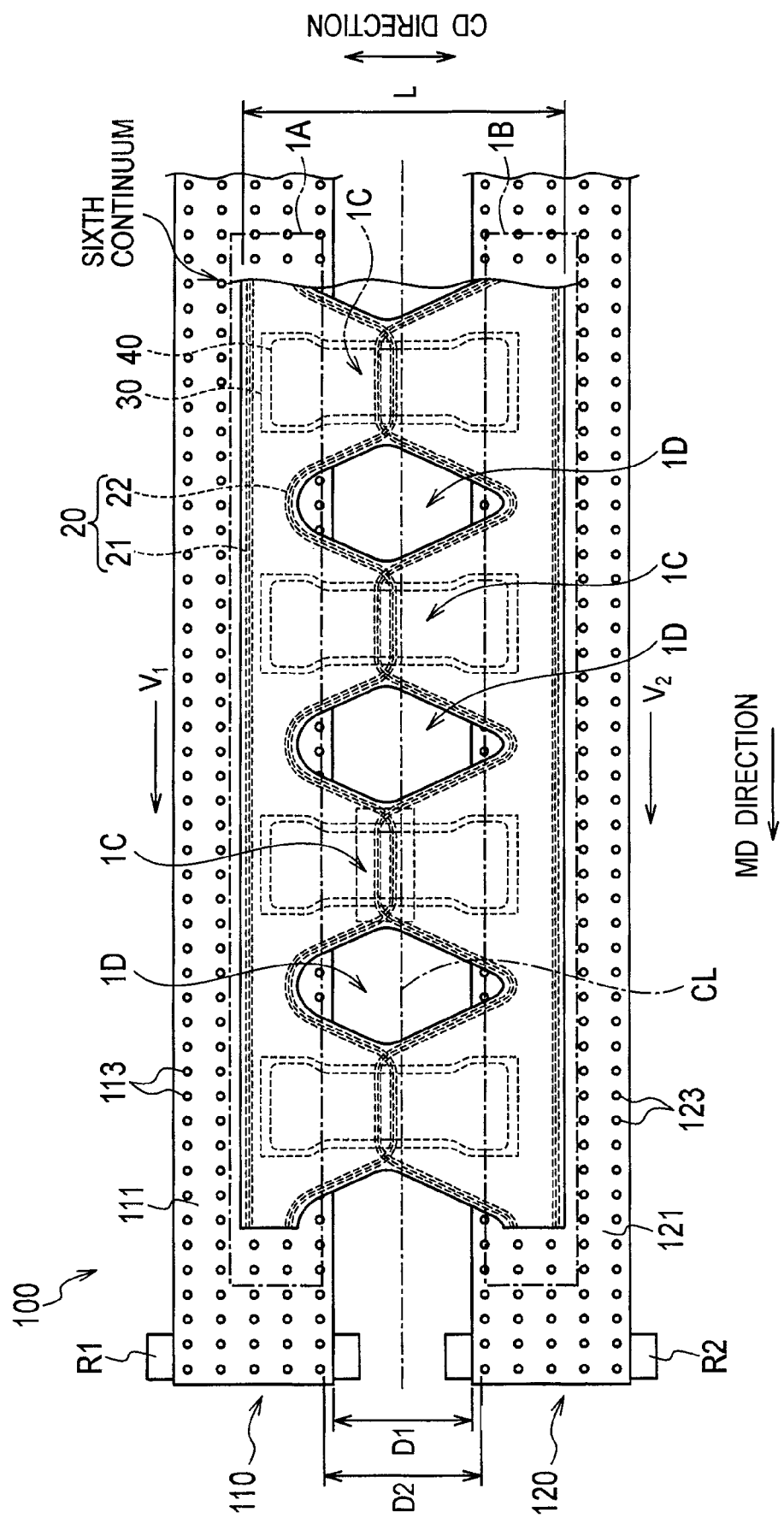
FIG. 4 is a partial top view showing the belt conveyor 100 according to the embodiment of the present invention (as viewed in the direction of the arrow A of FIG. 3).
Figure 5:
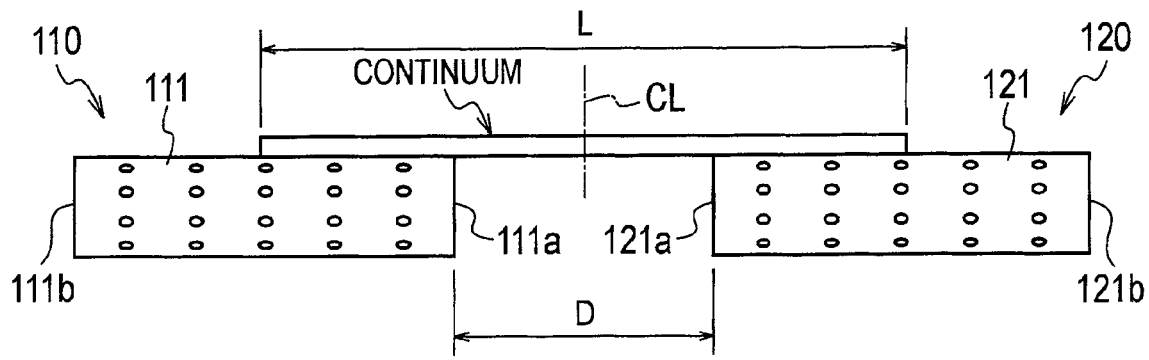
FIG. 5 is a front view showing the belt conveyor 100 according to the embodiment of the present invention (as viewed in the direction of the arrow B of FIG. 3).

Description will now be given with reference to FIGS. 3 to 5 with regard to the configuration of the belt conveyor according to the embodiment. FIG. 3 is a partial perspective view showing the belt conveyor 100 according to the embodiment. FIG. 4 is a partial top view showing the belt conveyor 100 according to the embodiment (as viewed in the direction of the arrow A of FIG. 3). FIG. 5 is a front view showing the belt conveyor 100 according to the embodiment (as viewed in the direction of the arrow B of FIG. 3).

Here, as shown in FIG. 3, the above-mentioned first to seventh continuums include the waistband regions 1A and 1B corresponding to the waistband member (or a waistband portion) of the absorptive article, the crotch region 1C disposed between the waistband regions 1A and 1B, and the leg opening regions 1D located on both sides of each of the crotch region 1C.

The waistband regions 1A and 1B have stretching properties in the MD direction. Note that the waistband regions 1A and 1B have the stretching properties indicates, for example, the fit gather 21 is provided so that the waistband regions 1A and 1B are stretchable, and the continuum in itself is made of a sheet having stretching properties, or the like.

The crotch region 1C has stretching properties in the CD direction. For example, the leg gather 23 is provided so that the crotch region 1C is stretchable, and the continuum in itself is made of a sheet having stretching properties, or the like.

The first to seventh continuums transported in the first to seventh transport steps are asymmetric with respect to the moving-direction center line CL. Specifically, in the first to seventh continuums, a difference lies at least partially in any given symmetrical locations across the moving-direction center line CL.

The continuums are asymmetric when, for example, any of the following differences occurs between any given symmetrical locations across the moving-direction center line CL: a difference in stretching property and in stress of the first continuum, the gather 20 and others, a difference in the position of the gather 20, differences in the positions of the waterproof film 30 and the absorber 40, and differences in the shapes of the crotch region 1C and the leg opening region 1D.

Since all the belt conveyors 100 used in the second to sixth transport steps have the same configuration as mentioned above, description will be given taking as an example the belt conveyor 100 that transports the sixth continuum in the sixth transport step.

As shown in FIGS. 3 to 5, the belt conveyor 100 includes the first belt conveyor 110 that transports the waistband region 1A, and the second belt conveyor 120 that transports the waistband region 1B. Here, the waist band region 1A and the waistband region 1B are located on both sides of the moving-direction center line CL. Incidentally, the moving direction of the first belt conveyor 110 is the same as the moving direction of the second belt conveyor 120.

The first belt conveyor 110 includes at least a first belt 111 that winds around a plurality of rollers (e.g., a roller R1 and a roller not shown), a first driving means (not shown) for causing the first belt 111 to move by the plurality of rollers, and a first suction means 112 for sucking the outside air.

A plurality of first suction holes 113 is formed on the first belt 111. The first suction holes 113 are formed for sucking the waistband region 1A therethrough. In other words, the waistband region 1A is sucked by the suction force of the first suction means 112 through the first suction hole 113.

The second belt conveyor 120 includes at least a second belt 121 that winds around a plurality of rollers (e.g., a roller R2 and a roller not shown), a second driving means (not shown) for causing the second belt 121 to move by the roller R2, and a second suction means 122 for sucking the outside air.

A plurality of second suction holes 123 is formed on the first belt 111. The first suction holes 113 are formed for sucking the waistband region 1B therethrough. In other words, the waistband region 1B is sucked by the suction force of the second suction means 122 through the second suction hole 123.

A suction force for sucking the seventh continuum (the one waistband region 1A) through the first suction holes 113 of the first belt conveyor 110 may be the same as or different from a suction force for sucking the seventh continuum (the other waistband region 1B) through the second suction holes 123 of the second belt conveyor.

The first belt 111 and the second belt 121 are disposed horizontal to a supporting surface (not shown) of the belt conveyor 100. Also, a distance D1 between the first belt 111 and the second belt 121 is fixed.

The distance D1 between the first belt 111 and the second belt 121 may be changed in accordance with a length L of the absorptive article (or the continuum) in the CD direction. Further, a distance D2 between the first suction hole 113 closest to the moving-direction center line CL and the second suction hole 123 closest to the moving-direction center line CL may be changed in accordance with the length of the absorptive article in the CD direction.

A traveling velocity $V_1$ of the first belt conveyor 110 may be the same as or different from a traveling velocity $V_2$ of the second belt conveyor 120.

(4) Operations and Effects

Generally, the manufacturing method for an absorptive article has difficulty in stably transporting the continuum. Specifically, to provide a comfortable fit, the absorptive article is required to have the property of stretching in the CD direction in addition to the property of stretching in the MD direction. Further, the absorber 40 is disposed on the side on which a liquid such as urine is discharged (e.g., on the side of the waistband region 1A).

Thus, in a method (namely, the cross feed method) in which the continuum is transported while the waistband front-back direction is in line with the CD direction, the continuum is asymmetric with respect to the moving-direction center line CL.

Therefore, in the embodiment, the continuum (the second to seventh continuums) that is asymmetric with respect to the moving-direction center line CL is transported while being held on the first belt conveyor 110 and the second belt conveyor 120. This allows stably transporting the continuum that is asymmetric in the CD direction as well as in the MD direction, thereby meandering of the continuum can be suppressed.

Specifically, one of the waistband regions (the waistband region 1A) on one side of the moving-direction center line CL is transported by the first belt conveyor 110, while the waistband regions (the waistband region 1B) on the other side of the moving-direction center line CL is transported by the second belt conveyor 120. This allows individual control of, for example, the traveling velocity, the force of attraction, or the like, since the first belt conveyor 110 and the second belt conveyor 120 are independent from each other. Therefore, displacement of the continuum on either side of the moving-direction center line CL can be prevented and thereby the meandering of the continuum can be suppressed, even when the continuum is transported as being asymmetric with respect to the moving-direction center line CL. Thus, a failure in the manufacture of the absorptive article can be prevented.

Moreover, since the first belt conveyor 110 and the second belt conveyor 120 are independent from each other, a camera or the like for quality control may be disposed, for example, between the first belt conveyor 110 and the second belt conveyor 120.

Furthermore, the continuum (the second to seventh continuums) that is asymmetric with respect to the moving-direction center line CL is transported while being held on the first belt conveyor 110 and the second belt conveyor 120 by the suction through the first suction holes 113 and the second suction holes 123. Accordingly, displacement of the continuum on either side of the moving-direction center line CL can be prevented and thereby the meandering of the continuum the meandering of the continuum can be further suppressed.

Additionally, when the suction force of the first belt conveyor 110 is different from the suction force of the second belt conveyor 120, or when the traveling velocity $V_1$ of the first belt conveyor 110 is different from the traveling velocity $V_2$ of the second belt conveyor 120, the first belt conveyor 110 and the second belt conveyor 120 may be controlled independently from each other. Further, when the distance D1 between the first belt 111 and the second belt 121 or the distance D2 between the first suction hole 113 closest to the moving-direction center line CL and the second suction hole 123 closest the moving-direction center line CL is changed in accordance with the length L of the absorptive article (or the continuum) in the CD direction, the first belt conveyor 110 and the second belt conveyor 120 may be controlled independently from each other. Therefore, this manufacturing method is adaptable to various continuums, thus increasing the general versatility of the first belt conveyor 110 and the second belt conveyor 120.

In particular, when the continuum is asymmetric with respect to the moving-direction center line CL, a configuration in which the suction force of the first belt conveyor 110 is different from the suction force of the second belt conveyor 120 is more suitable, than a configuration in which these suction forces of the first belt conveyor 110 and the second belt conveyor 120 are the same. Therefore, the meandering of the continuum can be further suppressed.

(5) Modified Embodiments

The belt conveyor 100 according to the above-mentioned embodiment may be modified as follows. Incidentally, the same parts as those of the belt conveyor 100 according to the above-mentioned embodiment are designated by the same reference numerals, and different parts will be mainly described.

(5-1) First Modified Embodiment

Figure 6:
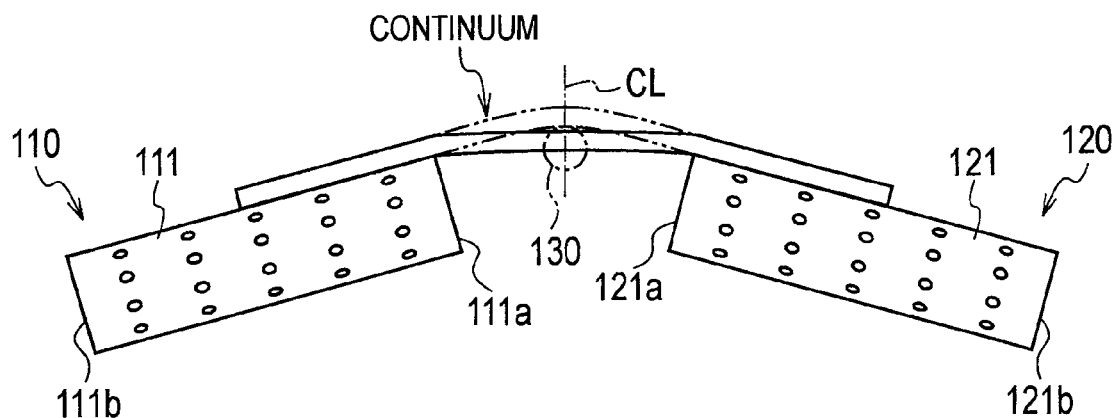
FIG. 6 is a front view (Part 1) showing the belt conveyor 100 according to a first modified embodiment (as viewed in the direction of the arrow B of FIG. 3).
Figure 7:
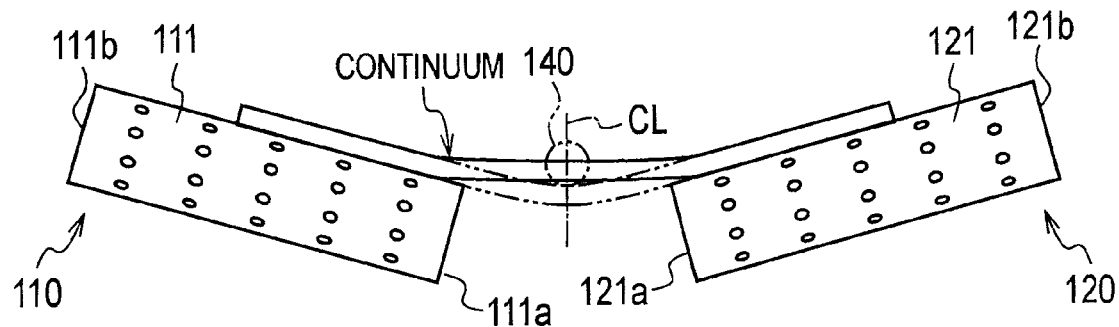
FIG. 7 is a front view (Part 2) showing the belt conveyor 100 according to the first modified embodiment (as viewed in the direction of the arrow B of FIG. 3).

Firstly, description will be given with reference to FIGS. 6 and 7 with regard to the configuration of the belt conveyor 100 according to a first modified embodiment. FIGS. 6 and 7 are front views showing the belt conveyor 100 according to the first modified embodiment (as viewed in the direction of the arrow B of FIG. 3).

The first belt 111 and the second belt 121 according to the above-mentioned embodiment are disposed horizontal to the supporting surface (the CD direction) of the belt conveyor 100. On the contrary, in the first modified embodiment, the first belt 111 and the second belt 121 are disposed as inclined on either side with respect to the supporting surface of the belt conveyor 100.

Specifically, as shown in FIG. 6, the first belt 111 of the first belt conveyor 110 is configured so that an end 111a located on the moving-direction center line CL side is positioned high while an end 111b located on the opposite side is positioned low. In the same manner, the second belt 121 of the second belt conveyor 120 is configured so that an end 121a located on the moving-direction center line CL side is positioned high while an end 121b located on the opposite side is positioned low.

In the first modified embodiment described above, the ends 111a and 121a are positioned high while the ends 111b and 121b are positioned low. Accordingly, the stress of the continuum in the CD direction can be suppressed. Thus, the meandering of the continuum can be further suppressed.

Incidentally, a guide member 130 (e.g., a bar-shaped member) configured to guide the continuum on the moving-direction center line CL may be provided between the first belt 111 and the second belt 121. In this case, when being transported, the continuum may be stretched outwardly of the continuum in the CD direction. In other words, a wrinkle can be prevented from occurring in the vicinity of the moving-direction center line CL.

Here, the first belt 111 and the second belt 121 are not necessarily configured such that the ends 111a and 121a located on the moving-direction center line CL side is positioned high. Alternatively, as a matter of course, the first belt 111 and the second belt 121 may be configured such that the ends 111a and 121a located the moving-direction center line CL side is positioned low, as shown in FIG. 7. This makes an advantage in the folding step described with reference to the above embodiment.

Incidentally, a guide member 140 (e.g., a bar-shaped member) configured to guide the continuum on the moving-direction center line CL may be provided between the first belt 111 and the second belt 121. In this case, when being transported, the continuum may be stretched outwardly of the continuum in the CD direction. In other words, a wrinkle can be prevented from occurring in the vicinity of the moving-direction center line CL.

(5-2) Second Modified Embodiment

Figure 8:
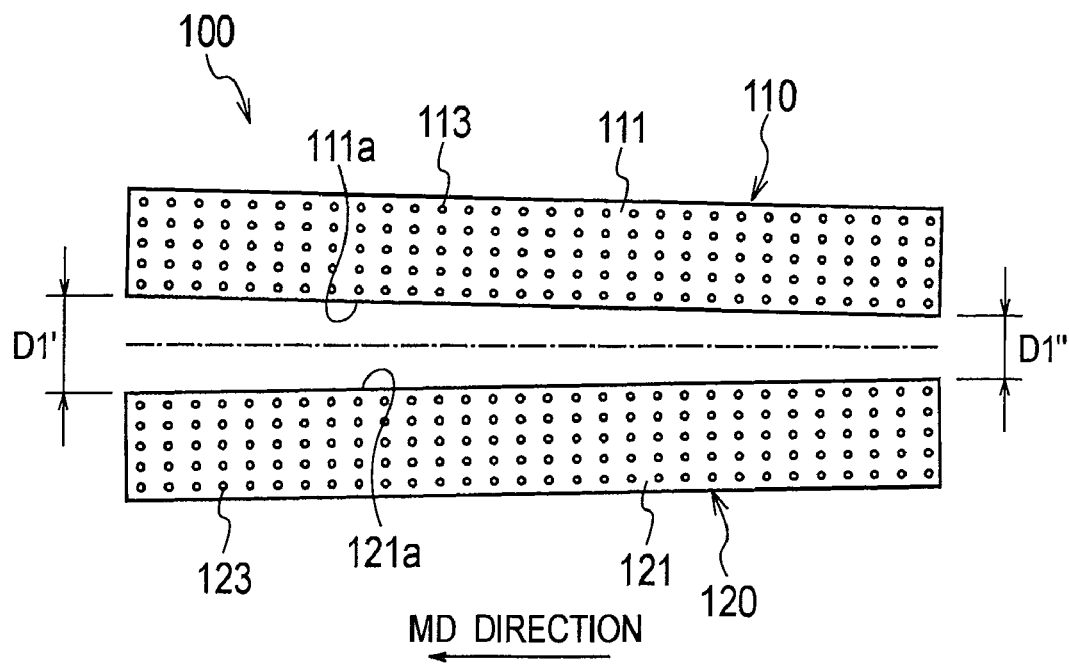
FIG. 8 is a partial top view (Part 1) showing the belt conveyor 100 according to a second modified embodiment (as viewed in the direction of the arrow A of FIG. 3).
Figure 9:
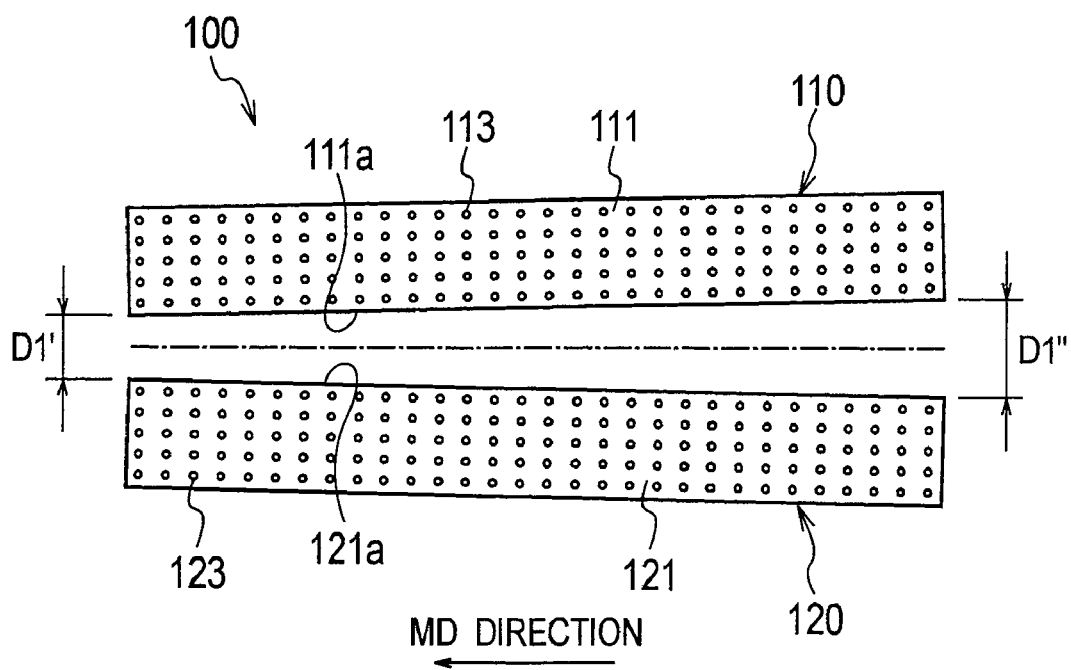
FIG. 9 is a partial top view (Part 2) showing the belt conveyor 100 according to the second modified embodiment (as viewed in the direction of the arrow A of FIG. 3).

Description will now be given with reference to FIGS. 8 and 9 with regard to the configuration of the belt conveyor 100 according to a second modified embodiment. FIGS. 8 and 9 are partial top views showing the belt conveyor 100 according to the second modified embodiment (as viewed in the direction of the arrow A of FIG. 3).

The moving directions of the first belt conveyor 110 and the second belt conveyor 120 according to the above-mentioned embodiment are the same. In other words, the distance D1 between the first belt 111 and the second belt 121 according to the above embodiment is fixed. On the contrary, the moving directions of the first belt conveyor 110 and the second belt conveyor 120 according to the second modified embodiment are different. In other words, distances D1' and D1" between the first belt 111 and the second belt 121 according to the second modified embodiment are not fixed.

Specifically, in the distance D1 between the end 111a of the first belt 111 and the end 121a of the second belt 121, the distance D1' toward the front of the belt conveyor 100 in the MD direction is longer than the distance D1" toward the rear side of the belt conveyor 100 in the MD direction.

In the first modified embodiment described above, the distance D1' is longer than the distance D1". Accordingly, when being transported, the continuum can be stretched outwardly of the continuum in the CD direction. In other words, a wrinkle can be prevented from occurring in the vicinity of the moving-direction center line CL.

Here, the distance D1' does not need to be longer than the distance D1", and the distance D1' may of course be shorter than the distance D1" as shown in FIG. 9. This makes an advantage in the folding step described with reference to the above embodiment.

(5-3) Third Modified Embodiment

Figure 10:
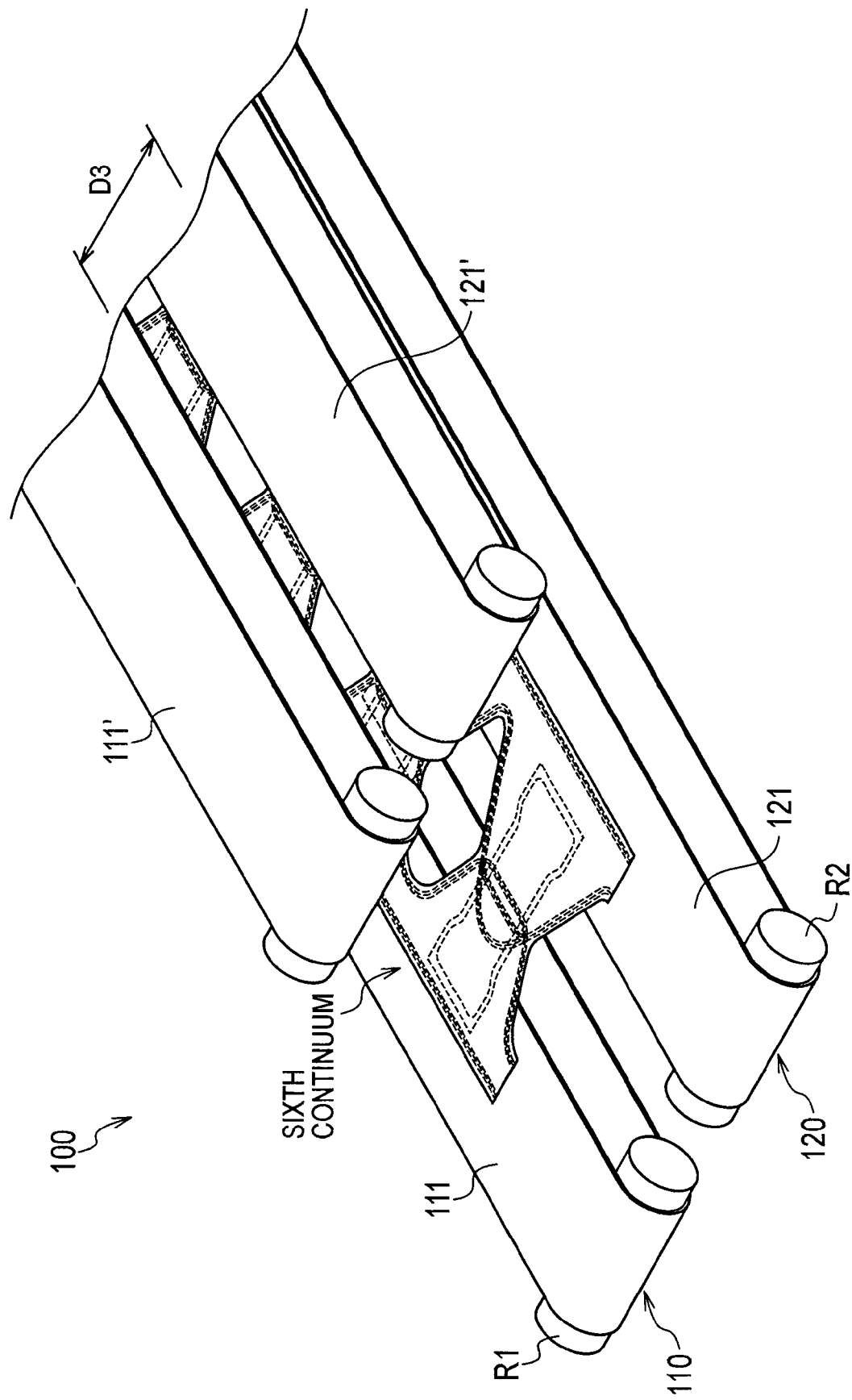
FIG. 10 is a partial perspective view showing the belt conveyor 100 according to a third modified embodiment.

Description will now be given with reference to FIG. 10 with regard to the configuration of the belt conveyor 100 according to a third modified embodiment. FIG. 10 is a partial perspective view showing the belt conveyor 100 according to the third modified embodiment.

According to the above-mentioned embodiment, the first belt conveyor 110 includes the first belt 111, and the second belt conveyor 120 includes the second belt 121. On the contrary, according to the third modified embodiment, the first belt conveyor 110 includes a pair of first belts 111 and 111', while the second belt conveyor 120 includes a pair of second belts 121 and 121'.

Specifically, as shown in FIG. 10, the first belt 111' is disposed on one side of the first belt 111 on which the continuum is transported (e.g., on the upper side in FIG. 10). In other words, the first belts 111 and 111' transport the continuum, while nipping therebetween the waistband region 1A disposed on one side of the moving-direction center line CL.

The second belt 121' is disposed on the side of the second belt 121 on which the continuum is transported (e.g., on the upper side in FIG. 10). In other words, the second belts 121 and 121' transport the continuum, while nipping therebetween the waistband region 1B disposed on the other side of the moving-direction center line CL.

Here, a distance (D3) between a first overlapping portion of the first belts 111 and 111' (in orthogonal direction) on the moving-direction center line CL side and a second vertical overlapping portion of the second belts 121 and 121' (in orthogonal direction) on the moving-direction center line CL side may be changed in accordance with the length L of the absorptive article (or the continuum) in the direction crossing the moving direction of the continuum.

In the third modified embodiment, the continuum is transported while being nipped between each of the pair of belts (the first belts 111 and 111'), and between each of the pair of belts (the second belts 121 and 121'). This eliminates the need for providing the suction holes in the first belt 111 and the second belt 121, and also eliminates the need for providing the suction means. Thus, the meandering of the continuum can be further suppressed.

Further, the configuration in which the distance (D3) between the first overlapping portion on the moving-direction center line CL side and the second overlapping portion on the moving-direction center line CL side can be changed in accordance with the length L of the absorptive article (or the continuum) is adaptable to various continuums. Thus, the general versatility of the first belt conveyor 110 and the second belt conveyor 120 can be further increased.

(6) Other Embodiments

Although the disclosure of the present invention has been given by way of the embodiments of the present invention as mentioned above, it is to be understood that the description and drawings that form part of this disclosure are not intended to limit the scope of the invention.

Specifically, the belt conveyor 100 has been described as including the first belt conveyor 110 and the second belt conveyor 120; however, the belt conveyor 100 is not limited to this and may include three or more belt conveyors, as a matter of course.

Incidentally, the belt conveyor 100 (the first belt conveyor 110 and the second belt conveyor 120) has been described as being used in the second to tenth transport steps; however, the belt conveyor 100 is not limited to this and may be used in at least one transport step, as a matter of course. Incidentally, the belt conveyor 100 may be used when the continuum is asymmetric with respect to the moving-direction center line CL, besides the steps described with reference to the above embodiment.

Further, the manufacturing method for an absorptive article has been described as including the steps in order from the gather step to the top sheet step; however, the method is not limited to this and may include the steps in order from the top sheet step to the gather step, as a matter of course.

Further, it is needless to say that, in the manufacturing method for an absorptive article, the folding step may be followed by any one of a bonding step of bonding partially the waistband regions 1A and 1B and a product cutting step of manufacturing a final product of the absorptive article by cutting the continuum into individual sizes.

For example when the continuum transported after the bonding step or the absorptive article transported after the product cutting step is asymmetric with respect to the moving-direction center line CL, the belt conveyor 100 (the first belt conveyor 110 and the second belt conveyor 120) mentioned above may be used.

Further, the absorptive article shown in FIGS. 3 and 4 includes the waistband regions 1A and 1B and the crotch region 1C that are integral with each other. However, the absorptive article is not limited to this and may include the waistband regions 1A and 1B and the crotch region 1C formed separate from each other.

From this disclosure, various alternative embodiments, examples and practical technologies will be obvious to those skilled in the art. It is to be therefore understood that the technological scope of the invention is determined only by claimed elements according to the scope of claims reasonably understood from the foregoing description.

What is claimed is:

1. A method of manufacturing an absorptive article having a waistband member, comprising:

transporting a continuum including waistband regions corresponding to the waistband member, wherein
in the transporting, the continuum has a shape asymmetric with respect to a center line that bisects a dimension of the continuum in cross direction that is perpendicular to a moving direction of the continuum,
the continuum is transported while being held on at least a first belt conveyor and a second belt conveyor,
the first belt conveyor includes a first belt including a plurality of first suction holes for sucking the continuum,
the second belt conveyor includes a second belt including a plurality of second suction holes for sucking the continuum,
in the transporting, the continuum is transported while being held by a suction force through the first suction holes and the second suction holes, and
a suction force for sucking the continuum through the plurality of first suction holes is different from a suction force for sucking the continuum through the plurality of second suction holes.

2. The method according to claim 1, wherein,
said waistband regions have first and second regions, and
in the transporting, the first waistband regions disposed on one side of the center line is transported by the first belt conveyor, while the second of the waistband regions disposed on the other side of the center line is transported by the second belt conveyor.

3. The method according to claim 1, wherein a distance between the first suction hole closest to the center line and the second suction hole closest to the center line is changed in accordance with the dimension of the absorptive article in the cross direction.

4. The method according to claim 1, wherein, in the transporting, the continuum is transported while being nipped between a pair of first belts of the first belt conveyor, and between a pair of second belts of the second belt conveyor.

5. The method according to claim 4, wherein a distance between an overlapping portion of the pair of first belts at one side of the center line and an overlapping portion of the pair of second belts at the other side of the center line is changed in accordance with the dimension of the absorptive article in the cross direction.

6. The method according to claim 1, wherein a distance between the first belt of the first belt conveyor and the second belt of the second belt conveyor is changed in accordance with the dimension of the absorptive article in the cross direction.

7. The method according to claim 1, wherein the first belt of the first belt conveyor and the second belt of the second belt conveyor are inclined with respect to the cross direction.

8. The method according to claim 1, wherein a moving direction of the first belt conveyor is different from a moving direction of the second belt conveyor.

9. The method according to claim 1, wherein
the waistband regions have first and second waistband regions,
the absorptive article is a disposable diaper provided with a crotch region located between the first waistband region and the second waistband region,
the waistband regions is stretchable in the moving direction, and the crotch region is stretchable in the cross direction.

10. The method according to claim 1, wherein the continuum includes an absorber configured to absorb liquid, and the absorber is disposed asymmetrically with respect to the center line.

11. The method according to claim 1, wherein
the waistband regions have first and second waistband regions,
the absorptive article is a disposable diaper provided with a crotch region located between the first waistband region and the second waistband region, and leg opening regions located on both sides of the crotch region, and
the leg opening regions are formed asymmetrically with respect to the center line.

12. A method of manufacturing an absorptive article having a waistband member, comprising:
transporting a continuum including waistband regions corresponding to the waistband member,
wherein
in the transporting, the continuum has a shape asymmetric with respect to a center line that bisects a dimension of the continuum in cross direction that is perpendicular to a moving direction of the continuum,
the continuum is transported while being held on at least a first belt conveyor and a second belt conveyor,
wherein a traveling velocity of the first belt conveyor is different from a traveling velocity of the second belt conveyor.

13. The method according to claim 12, wherein,
said waistband regions have first and second regions, and
in the transporting, the first waistband regions disposed on one side of the center line is transported by the first belt conveyor, while the second of the waistband regions disposed on the other side of the center line is transported by the second belt conveyor.

* * * * *